United States Patent
Schiller

(10) Patent No.: US 6,703,483 B1
(45) Date of Patent: Mar. 9, 2004

(54) COMPOUNDS USEFUL IN PAIN MANAGEMENT

(75) Inventor: Peter Schiller, Montreal (CA)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/590,165

(22) PCT Filed: Mar. 8, 2000

(86) PCT No.: PCT/SE00/00462

§ 371 (c)(1),
(2), (4) Date: Jun. 9, 2000

(87) PCT Pub. No.: WO00/55189

PCT Pub. Date: Sep. 21, 2000

(30) Foreign Application Priority Data

Mar. 16, 1999 (SE) .............................. 9900961

(51) Int. Cl.$^7$ ................................ C07K 5/10
(52) U.S. Cl. ........................ 530/330; 514/18
(58) Field of Search ................ 530/330; 514/18

(56) References Cited

U.S. PATENT DOCUMENTS

| | | | | |
|---|---|---|---|---|
| 5,312,899 A | * | 5/1994 | Schiller | 530/331 |
| 5,602,100 A | * | 2/1997 | Brown | 514/18 |
| 5,885,958 A | * | 3/1999 | Zadina | 514/9 |
| 5,994,372 A | * | 11/1999 | Yaksh | 514/327 |

FOREIGN PATENT DOCUMENTS

WO  WO 95/22557  8/1995

OTHER PUBLICATIONS

Clapp, et al., "Cardiovascular and Metabolic Responses to Two Receptor–Selective Opioid Agonists in Pregnant Sheep," *Am. J. Obstet. Gynecol.* 178:397–401 (1998).

DiMaio, et al., "Synthesis and Pharmacological Characterization in Vitro of Cyclic Enkephalin Analogues: Effect of Conformational Constraints on Opiate Receptor Selectivity," *J. Med. Chem.* 25:1432–1438 (1982).

Majer, et al., "Synthesis of Methylated Phenylalanines Via Hydrogenolysis of Corresponding 1,2,3, 4–Tetrahydroisoquinoline–3–Carboxylic Acids," *Int. J. Peptide Protein Res.* 43:62–68 (1994).

Schiller, et al., "Dermorphin Analogues Carrying an Increased Positive Net Charge in Their 'Message' Domain Display Extremely High μ Opioid Receptor Selectively," *J. Med. Chem.* 32:698–703 (1989).

Schiller, et al., "TIPP[ψ]: A Highly Potent and Stable Pseudopeptide δ Opioid Receptor Antagonist with Extraordinary δ Selectivity," *J. Med. Chem.* 36:3182–3187 (1993).

Schiller et al., "Unsulfated C–Terminal 7–Peptide of Cholecystokinin: A New Ligand of the Opiate Receptor," *Biochem. Biophys. Res. Comm.* 85:1332–1338 (1978).

Schiller, et al., "Opioid Peptide Analogs with Novel Activity Profiles as Potential Therapeutic Agents for use in Analagesia," *Pept. Sci.: Present Future, Proc. 1$^{st}$ Int. Pept. Symp.* (1999), Meeting Date 1997, 665–669.

* cited by examiner

Primary Examiner—Christopher S. F. Low
Assistant Examiner—David Lukton
(74) Attorney, Agent, or Firm—Michael A. Sanzo; Fitch, Even, Tabin & Flannery

(57) ABSTRACT

Compounds of the formula I

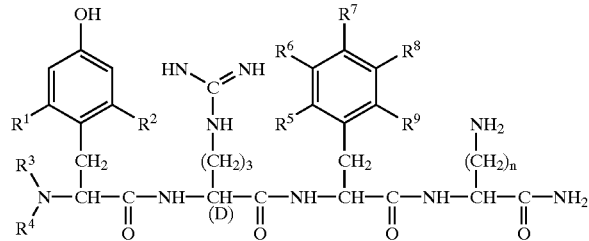

are disclosed and claimed in the present application, as well as their pharmaceutically acceptable salts, pharmaceutical compositions comprising the novel compounds and their use in therapy, particular in the management of pain, and more particularly in the management of pain during labor.

9 Claims, No Drawings

COMPOUNDS USEFUL IN PAIN MANAGEMENT

CROSS REFERENCE TO RELATED APPLICATIONS

The present application represents U.S. national stage of international application PCT/SE00/00462, with an international filing date of Mar. 8, 2000, and which was published in English under Article 21(2) of the PCT on Sep. 21, 2000. The international application claims priority to Swedish application 9900961-5, filed Mar. 16, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain during labor.

BACKGROUND AND PRIOR ART

Although a wide spectrum of narcotics are now available, only a few are used currently in obstetrics, including morphine, pethidine, fentanyl and sufentanil. These narcotics can cause a variety of side effects in the mother, including respiratory depression, and orthostatic hypotension. Furthermore, because of their, lipophilic character, these opiate analgesics are transferred rapidly across the placenta and often produce neonatal respiratory depression and changes in the neurobehavior of the child. While these side effects are particularly pronounced when lipophilic opiates are administered systemically, they are still of some concern with the delivery of classical narcotics by the spinal or epidural route which were introduced in 1979 and are now widely accepted for obstetric analgesia.

Opioid peptides and their analogs have a reduced ability to cross the placental barrier because of their polar character. A number of opioid peptide analogs with high selectivity for $\mu$ opioid receptors and $\mu$ agonist properties have been developed (for a review, see P. W. Schiller, in *"Progress in Medicinal Chemistry"*, Vol. 28 (G. P. Ellis and G. B. West, eds.), Elsevier, Amsterdam, The Netherlands, 1991, pp. 301–340). Among these, the dermorphin related tetrapeptide analog H-Tyr-D-Arg-Phe-Lys-NH$_2$ (DALDA) is particularly polar (P. W. Schiller et al., *J. Med. Chem.* 32, 698–703 (1989)). DALDA is also disclosed and claimed in U.S. Pat. No. 5,312,899, granted May 17, 1994 to P. W. Schiller and now assigned to the Applicant of the present application. DALDA shows high $\mu$ receptor affinity and excellent $\mu$ receptor selectivity in the rat brain membrane binding assay as well as considerable $\mu$ agonist potency in the functional guinea pig ileum (GPI) bioassay. However, like morphine, DALDA did produce delayed respiratory depression (2 h after i.th. administration) at a dose of 7.5 $\mu$g (32×ED50).

The problem underlying the present invention was thus to provide novel compounds with improved $\mu$ agonist potency, as well as with as few side-effects as possible. More particularly the object of the invention was to improve the potency as well as the side-effect profile for compounds used particularly within the obstetrics field.

Outline of the Invention

The present invention is directed to novel analogs of DALDA, defined by the formula I

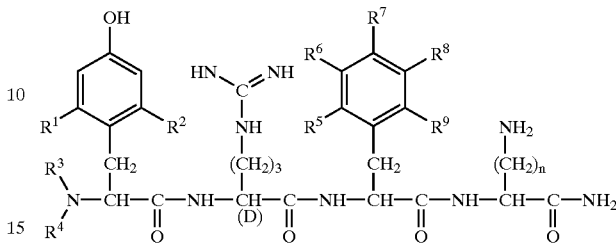

wherein
$R^1$ is selected from
  (i) linear or branched $C_1$–$C_6$ alkyl;
  (ii) $C_1$–$C_6$ alkoxy;
$R^2$ is selected from
  (i) hydrogen;
  (ii) linear or branched $C_1$–$C_6$ alkyl;
  (iii) $C_1$–$C_6$ alkoxy;
$R^3$ and $R^4$ is each and independently selected from
  (i) hydrogen;
  (ii) linear or branched $C_1$–$C_6$ alkyl;

(iii) —(CH$_2$)$_m$—phenyl   wherein m = 1–3;

(iv) —CH$_2$—cyclopropyl;   and (v) —CH$_2$—CH═CH$_2$;

$R^5$, $R^6$, $R^7$, $R^8$ and $R^9$ is each and independently selected from
  (i) hydrogen;
  (ii) halogen, where "halogen" encompasses chloro, fluoro, bromo and iodo; and
  (iii) linear or branched $C_1$–$C_6$ alkyl; and
  n is an integer of from 1 to 5.
In a preferred embodiment of the present invention
$R^1$ is a linear $C_1$–$C_6$ alkyl;
$R^2$ is a linear $C_1$–$C_6$ alkyl or hydrogen;
$R^3$ and $R^4$ is each and independently selected from a straight $C_1$–$C_6$ alkyl or hydrogen;
$R^5$, $R^6$, $R^7$, $R^8$ and $R^9$ is each and independently selected from
  (i) hydrogen;
  (ii) halogen, where "halogen" encompasses chloro, fluoro, bromo and iodo;
  (iii) linear or branched $C_1$–$C_6$ alkyl; and
  n is an integer of from 1 to 5.
In a particularly preferred embodiment of the present invention
$R^1$ is $CH_3$;
$R^2$ is hydrogen or $CH_3$;
$R^3$ and $R^4$ are both hydrogen; and $R^5$, $R^6$, $R^7$, $R^8$ and $R^9$ are all hydrogen; and n is 4.

Within the scope of the invention are also pharmaceutically acceptable salts of the compounds of the formula I.

Suitable pharmaceutically acceptable salts of the compounds of formula I are the hydrochloride salt, the acetate salt and the trifluoroacetate salt.

The novel compounds of the present invention, which compounds are DALDA analogs, are useful in therapy, especially as analgesics, and particularly as analgesics within the field of obstetrics. The wording "analgesics" is defined as absence of pain in response to stimulation which would normally be painful.

Also within the scope of the invention is the use of a compound of the formula I above, for the manufacture of a medicament for use as an analgesic, particularly as an analgesic within the field of obstetrics, more particularly for use in the treatment of pain during labor.

A further aspect of the invention is a method for the treatment of a subject suffering from pain, particularly pain during labor, whereby an effective amount of a compound of the formula I above, is administered to a patient in need of pain relief.

Methods of Preparation

The compounds of the present invention may be prepared as described in the following.

Most Boc-amino acid derivatives used in the peptide syntheses are commercially available (Bachem Bioscience and RSP Amino Acid Analogues). 2-methyl-L-tyrosine (Mmt) was prepared by hydrogenolysis of 7-hydroxytetrahydroisoquinoline-3-carboxylic acid using Pd/$H_2$ as described by P. Majer et al., *Int. J. Peptide Protein Res.* 43, 62–68 (1994).

All peptides were prepared by solid-phase techniques. The p-methylbenzhydrylamine resin was used for the solid-phase synthesis of the peptides which all contain a C-terminal carboxamide group. Boc protection of the amino group was employed in the preparation of all peptides. The syntheses were performed according to protocols that have been extensively used in the inventor's laboratory (P. W. Schiller et al. *J. Med. Chem.* 36. 3182–3187 (1993)). Couplings were performed in a mixture of $CH_2Cl_2$/DMF (95:5; v/v), using 1,3-diisopropylcarbodiimide (DIC)/1-hydroxybenzotriazole (HOBt) as coupling agents. Completeness of coupling was carefully examined after each coupling step by means of the ninhydrin color test. The fully assembled peptide was cleaved from the resin and completely deprotected by treatment with liquid HF at 0° C. and in the presence of anisole as scavenger (60–90 min).

The HPLC system GOLD (Beckman) consisting of the programmable solvent module 126 and the diode array detector module 168 was used in the purification and the purity control of the peptides. Reversed-phase HPLC was performed using a gradient made from two solvents: (A) 0.1% TFA in water and (B) 0.1% TFA in acetonitrile. For preparative runs a Vidac 218TP1022 column (250×22 mm) was used with a linear gradient of 5–20% B over a period of 30 min at a flow rate of 7 mil/min, absorptions being measured at both 216 nm and 280 nm. The same gradient was used for analytical runs on a Vidac 218TP0046 column (250×4.6 mm) over a period of 30 min at a flow rate of 1.0 ml/min. Purity of peptides was also established by TLC on precoated silica gel plates 60F-254 (E. Merck, Darmstadt, Germany) in the following solvent systems (all v/v): (A) n-BuOH/AcOH/$H_2O$ (4:1:5, organic phase) and (B) n-BuOH/pyridine/AcOH/$H_2O$ (15:10:3;12). Peptides were visualized with UV and with the ninhydrin spray reagent. Molecular weights of peptides were determined by FAB mass spectrometry on an MS-50 HMTCTA mass spectrometer interfaced with a DS-90 data system.

EXAMPLES

The invention will now be described in more detail by way of the following Examples, which are not to be construed as limiting the invention in any way.

Example 1

Preparation of H-Dmt-D-Arg-Phe-Lys-$NH_2$

Benzhydrylamine resin (1 g, 0.54 meq/g resin, Bachem Bioscience) was washed with reagents in the following sequence: $CH_2Cl_2$ (3×1 min), 10% (v/v) DIEA in $CH_2Cl_2$ (2×5 min), $CH_2Cl_2$ (5×1 min). Boc-Lys(2-Cl—Z) (560 mg, 1.35 mmol) was then coupled using HOBt (182 mg, 1.35 mmol) and DIC (170 mg, 1.35 mmol) in $CH_2Cl_2$/DMF (95:5, v/v) for 3 h. The resin was then washed with $CH_2Cl_2$ (3×1 min), EtOH (1 min) and $CH_2Cl_2$ (3×1 min). The resin was then treated with 50% (v/v) TFA in $CH_2Cl_2$ (30 min). This sequence of washes and reactions was repeated for the addition of each of the residues. The following side chain-protected Boc-amino acids were used: Boc-D-Arg(Tos)-OH and Boc-Dmt-OH. After final deprotection with 50% (v/v) TFA in $CH_2Cl_2$ (30 min), the resin was washed with $CH_2Cl_2$ (3×1 min) and ETOH (3×1 min) and was dried in a dessicator. The dry resin was treated with 20 ml of HF plus 1 ml of anisole first for 90 min at 0° C. and then for 15 min at room temperature. After evaporation of the HF, the resin was extracted three times with $Et_2O$ and, subsequently three times with 1M AcOH. The crude peptide was then obtained in solid form through lyophilization of the combined acetic acid extracts. The peptide was purified by HPLC on a Vidac 218TP1022 column (250×22 mm) with a linear gradient of 5–20% acetonitrile in 0.1% TFA. After solvent evaporation the pure peptide was dissolved in conc. AcOH and was obtained in solid form through lyophilization.

Yield: 200 mg (61%);

FAB—MS: $MH^+$=639;

TLC (silica): $R_f$=0.15 (A); $R_f$=0.28 (B);

HPLC: k'=2.05

Examples 2–4

By following the same procedure as described in Example 1 above, the compounds shown in Table 1 were also prepared.

TABLE 1

| Example | Compound | Molecular weight FAB-MS [$MH^+$] |
| --- | --- | --- |
| 2 | H-Dmt-D-Arg-Phe-Orn-$NH_2$ | 625 |
| 3 | H-Dmt-D-Arg-Phe-$A_2$bu-$NH_2$ | 611 |
| 4 | H-Mmt-D-Arg-Phe-Lys-$NH_2$ | 625 |
| 5 | H-Dmt-D-Arg-Phe(p-F)-Lys-$NH_2$ | 657 |
| 6 | Dmt(NMe)-D-Arg-Phe-Lys-$NH_2$ | 653 |

Pharmaceutical Compositions

Also within the scope of the present invention, are pharmaceutical compositions comprising a compound of formula I or a salt thereof as active ingredient, in admixture with one or more pharmaceuticaly acceptable carriers.

Suitable pharmaceutical compositions according to the present invention are pharmaceutical compositions in liquid form, suitable for administration intrathecally, epidurally, intramuscularly, and intravenously. Infusion is particularly preferred.

The dosage will depend on the severity of the pain, the patient's weight and other factors normally considered by the attending physician when determining the individual regimen and dosage level as the most appropriate for a particular patient.

Biological Evaluation

Pharmacologic Testing in Vitro of $\mu$ Opioid Agonists

Bioassays based on inhibition of electrically evoked contractions of the guinea pig ileum (GPI) and mouse vas deferens (MVD) were performed. In the GPI assay the opioid effect is primarily mediated by $\mu$ receptors, whereas in the MVD assay the inhibition of the contractions is mostly due to interaction with $\delta$ opioid receptors. Agonist potencies are expressed as IC50 values (concentration of the agonist that produces 50% inhibition of the electrically induced contraction).

Bioassays Using Isolated Oroan Preparations

The GPI and MVD bioassays were carried out as reported in P. W. Schiller et al., *Biochem. Biophys. Res. Commun.* 85, 1332–1338 (1978) and J. DiMaio et al., *J. Med. Chem.* 25, 1432–1438 (1982). A log-dose/response curve was determined with [Leu$^5$]enkephalin as standard for each ileum and vas preparation, and IC50 values of the compounds being tested were normalized according to A. A. Waterfield et al., *Eur. J. Pharmacol.* 58, pp. 11–18 (1997).

Opioid Receptor Binding Assays $\mu$ and $\delta$ receptor binding constants ($K_i^\mu, K_i^\delta$) of the compounds were determined by displacement of relatively selective $\mu$ and $\delta$ radioligands from binding sites in rat brain membrane preparations (calculated from the measured IC50 values on the basis of the equation by Cheng and Prusoff (Y. C. Cheng and W. H. Prusoff (*Biochem. Pharmaco.* 22, 3099–3102, 1973)). The ratio $K_i^\delta/K_i^\mu$ was a quantitative measure of the $\mu$ versus $\delta$ receptor selectivity. $\kappa$ receptor binding constants were determined by displacement of a $\kappa$ receptor-selective radioligand from guinea pig brain membrane preparations, since the relative proportion of $\kappa$ binding sites is higher in guinea pig brain than in rat brain.

Opioid Receptor Binding Experiments

The experimental procedure used represents a modified version of the binding assay described by Pasternak et al. (*Mol. Pharmacol.* 11, 340–351 (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris HCl, pH 7.7). After centrifugation at 30,000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [3H]DAMGO, $\mu$-selective, 0.7 nM; [$^3$H]DSLET, $\delta$-selective, 1.0 nM; and [$^3$H]U69,563, $\kappa$-selective, 0.5 nM. The incubation was terminated by filtration through Whatman GF/B filters under vacuum at 4° C. Following two washings with 5 ml portions of ice-cold buffer the filters were transferred to scintillation vials and treated with 1 ml Protosol (New England Nuclear) for 30 min prior to addition of 0.5 ml acetic acid and 10 ml Aquasol (New England Nuclear). After shaking for 30 min the vials were counted at an efficiency of 40–45%. All experiments were performed in duplicate and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of the specific binding were obtained graphically from semi-logarithmic plots. From the measured IC50-values, binding inhibition constants ($K_i$) were calculated based on Cheng and Prusoff's equation. Ratios of the $K_i$-values determined in the $\mu$-, $\delta$ and $\kappa$-representative binding assays are a measure of the receptor selectivity of the compound under investigation (e.g. $K_i^\delta/K_i^\mu$ indicates the selectivity for $\mu$-receptors versus $\delta$-receptors).

Analgesic Testing

The rat tail flick test was used to assess the antinociceptive effect of the compounds after intrathecal (i.th.) administration. Male Sprague-Dawley rats (300–350 g) were used. For the spinal administration of the compounds to the rat, a catheter was placed in the intrathecal space. Under general anesthesia, a PE-10 tube was threaded to the level of the lumbosacral spinal cord, as described in the literature (N. Shimoyama et al., *Anesthesiology* 85, 1357–1366 (1996)). Methylene blue staining and dissection at the end of the study confirmed the correct placement of the catheter.

In the tail flick test the antinociceptive potency of the compounds was determined by cumulative dose-response analysis (N. Shimoyama et al,*J. Pharmacol. Exp. Ther.* 283, 648–652 (1997)). Intrathecal doses of each drug were delivered in a volume of 5 $\mu$l followed by 10 $\mu$l of saline to flush the catheter. A tail-flick apparatus (EMDIE, Richmond, Va.) was used to apply radiant heat at 5 to 8 cm from the tip of the tail. The time from the onset of the heat stimulus to the withdrawal of the tail (tail-flick latency) was measured. The intensity of the radiant heat was adjusted such that the base-line latencies were between 2.5 and 3.5 sec. Subsequent response latencies were determined at 15 min after spinal delivery of the compound. To avoid tissue damage the heat stimulus was turned off after 10 sec (cut-off latency). After measuring the base-line latencies, increasing doses of the compound to be tested were administered until each animal became an analgesic responder (cumulative dose-response assessment, as described by K. Elliott et al., *Pain* 59, 361–368 (1994)) or reached the highest test dose. An analgesic responder was defined as one whose response tail-flick latency was 2 or more times the value of the base-line latency. The latency data were converted to a quantal form by determining the percentage of analgesic responders in each group for each cumulative dose, and a dose-response curve was constructed for each compound. The quantal dose-response data were analyzed with the BLISS-21 computer program. This program maximized the log-likelihood function to fit a Gaussian normal sigmoid curve to the dose-response data and provided the ED50 value and a 95% confidence interval (CI) (J. G. Umans and C. E. Inturrisi. *J. Pharmacol. Exp. Ther.* 218, 409–415 (1981)).

Respiratory Depression Studies (Whole Body Plethysmography)

Whole body plethysmography was performed as described in the literature (K. Tatsumi et al.,*J. Appl. Physiol.* 71, 37–42 (1991)). An unrestrained rat was placed in a 3-liter whole-body plethysmograph chamber and breathed 100% humidified air supplied into and out of the chamber at a rate of 1000 ml/min. After a 15-min acclimation period the inlet and outlet of the chamber were closed and the pressure changes in the box, caused by the warming and wetting of the gas inspired by the rat and the cooling and drying of the expired gas, were recorded using a high-gain differential pressure transducer. A calibration volume of 0.2 ml of air was regularly introduced into the chamber during the recordings. The recordings were made for 20–30 seconds. Subsequently, the inlet and outlet were opened, and the gas supply was changed to a mixture of 5% $CO_2$ and 21% $O_2$ in $N_2$ (100% humidified) and the rat was allowed to breathe the gas mixture for 5 min to reach a steady-state ventilatory condition. The recordings of changes in pressure were repeated with the chamber closed. Tidal volumes were calculated from the pressure changes using the equation derived by J. E. Drorbaugh and W. O. Fenn, *Pediatrics* 16, 81–87 (1955). Respiratory frequencies were also determined from the number of respiratory cycles in the recordings and minute ventilations were calculated (tidal volume x frequency).

Compounds were administered at a low dose (3×ED50 determined in the analgesic test) and at a high dose (30× ED50). The high dose of morphine and both the low and the high dose of DALDA significantly decreased minute ventilation by 26%, 26% and 30%, respectively, during a period of 3 to 6 hours after i.th. administration. Neither dose of H-Dmt-D-Arg-Phe-Lys-$NH_2$ significantly decreased minute ventilation as compared to the control value determined with saline.

In Vivo Disposition in Pregnant Sheep

The in vivo disposition after i.v. administration to pregnant sheep was examined by using procedures described in the literature (H. H. Szeto et al. *J. Pharmacol. Exp. Ther.* 284. 61–65 (1998)). Chronic indwelling catheters were surgically placed in four pregnant ewes (gestional age, 115–120 days; term ~145 days) as described by H. H. Szeto et al., *Am. J. Physiol.* 258, R1453–R1458 (1990). One polyvinyl catheter was inserted into the femoral artery and advanced to the distal aorta for blood sampling and another was advanced into the inferior vena cava via the femoral vein for drug infusion. A fetal hindlimb was exposed via hysterotomy incision, and chronic indwelling catheters were also placed in the fetal distal aorta and inferior vena cava. The compounds according to the invention were administered as a constant-rate intravenous infusion (0.6 mg/kg/h and 0.06 mg/kg/h, respectively, for 4 h) to the sheep, and blood samples were collected at 0, 1, 2, 3, 3.5, 4, 4.25, 4.5, 5, 6, 7, 12 and 24 h. Blood samples were collected form the fetus at 0, 3, 3.5, 4, 5 and 6 h. All blood samples were collected into chilled borosilicate glass tubes containing EDTA and centrifuged, and the plasma was stored in glass containers with Teflon-lined caps and frozen at −80° C.

The compounds were quantified by using reversed-phase HPLC and MS detection, as described by Grigoriants et al., *J. Chromatogr. B, Biomedical Applications* 695, 287–298 (1997). Plasma samples were deproteinated and eluted through a solid-phase extraction cartridge (Sep-Pak C18; Millipore) with $CH_3CN$. An internal standard, the deuterated DALDA analog H-Tyr-D-Arg-Phe($d_5$)-Lys-$NH_2$ or a deuterated analog of a compound according to the invention, was added to each plasma sample before deproteinization. The filtered plasma sample was chromatographed on an RP-analytical column (Delta Pak, 5 μm, C18, 100 Å, 150× 3.9 mm; Waters, Milford, Mass.) at a flow rate of 1.5 ml/min, and UV absorption was monitored at 200 nm. One-minute fractions were collected and each fraction was lyophilized for MS analysis (Auto SpecQ tandem mass spectrometer, Micromass, Altrincham, UK). Continuous flow-LSIMS was used to quantify DALDA. The (M+H)$^+$ ion current for DALDA at m/z 612 was compared with the ion current from $d_5$-DALDA at m/z 617, and the one for the DALDA analog at its m/z value was compared with the one from the deuterated DALDA-analog. The limit of sensitivity of this method is 50 mg/ml DALDA or DALDA analog.

Neither of the peptides was detected in any of the fetal plasma samples. In other words, DALDA and its analogs according to the present invention, do not cross the placental barrier to a significant extent.

Hemodynamic and Metabolic Effects of DALDA and its Analogs in the Pregnant Sheep Model Using the same instrumented pregnant sheep model described above, DALDA and its analogs were administered by i.v. infusion at a dose of 0.6 mg/kg/h and 0.06 mg/kg/h, respectively. No effect on maternal blood pressure, heart rate, blood gases and plasma glucose were observed. Similarly, neither peptide had any effect on fetal blood pressure, heart rate, blood gases and plasma glucose.

The best mode of performing the invention known at present is the use of the compound according to Example 1.

Abbreviations $A_2Bu$=(α, γ-diaminobutyric acid
Boc=tert-butoxycarbonyl
CI=confidence interval
DALDA=H-Tyr-D-Arg-Phe-Lys-$NH_2$
DAMGO=H-Tyr-D-Ala-Gly-Phe(NαMe)-Gly-ol
DIC=1,3-diisopropylcarbodiimide
Dmt=2′,6′-dimethyltyrosine
DSLET=H-Tyr-D-Ser-Gly-Phe-Leu-Thr-OH
EDTA=ethylenediaminetetraacetic acid
FAB—MS=fast atom bombardment mass spectrometry
GPI=guinea pig ileum
HOBt=1-hydroxybenzotriazole
HPLC=high performance liquid chromatography
i.th.=intrathecal
LSIMS=liquid secondary ion mass spectrometry
Mmt=2′-methyltyrosine
MS=mass spectrometry
MVD=mouse vas deferens
TFA=trifluoroacetic acid
TLC=thin layer chromatography
Tos=tosyl
U69,593=(5α, 7α, 8β)-(−)-N-methyl-[7-pyrrolidinyl)-1-oxaspiro[4,5]dec-8-yl]benzeneacetamide

What is claimed is:

1. A compound of formula I:

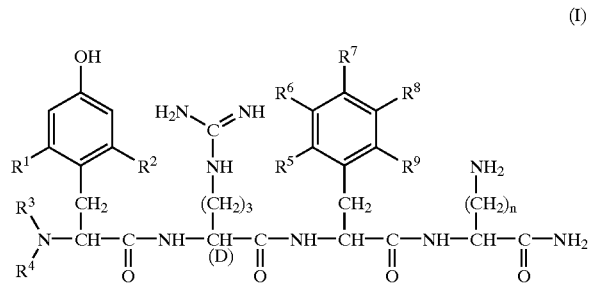

wherein
R$^1$ is selected from
(i) a linear or branched $C_1$–$C_6$ alkyl;
(ii) a $C_1$–$C_6$ alkoxy;

$R^2$ is selected from
(i) hydrogen;
(ii) a linear or branched $C_1$–$C_6$ alkyl;
(iii) a $C_1$–$C_6$ alkoxy;

$R^3$ and $R^4$ is each and independently selected from
(i) hydrogen;
(ii) a linear or branched $C_1$–$C_6$ alkyl;

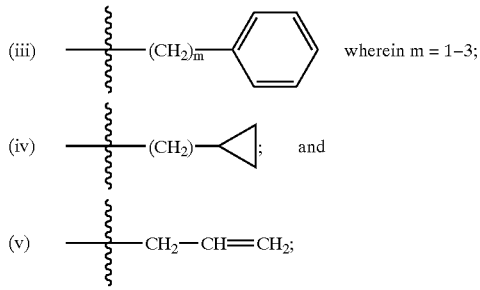

$R^5$, $R^6$, $R^7$, $R^8$ and $R^9$ is each and independently selected from
(i) hydrogen;
(ii) a halogen, wherein said halogen is selected from the group consisting of: chloro, fluoro, bromo and iodo; and
(iii) a linear or branched $C_1$–$C_6$ alkyl; and n is an integer of from 1 to 5;
or a pharmaceutically acceptable salt thereof.

2. A compound of formula I according to claim 1, wherein
$R^1$ is a linear $C_1$–$C_6$ alkyl;
$R^2$ is a linear $C_1$–$C_6$ alkyl or hydrogen;
$R^3$ and $R^4$ is each and independently selected from a straight $C_1$–$C_6$ alkyl or hydrogen;
$R^5$, $R^6$, $R^7$, $R^8$ and $R^9$ is each and independently selected from
(i) hydrogen;
(ii) halogen, where "halogen" encompasses chloro, fluoro, bromo and iodo;
(iii) linear or branched $C_1$–$C_6$ alkyl; and
n is an integer of from 1 to 5.

3. A compound according to claim 1, wherein
$R^1$ is $CH_3$;
$R^2$ is hydrogen or $CH_3$;
$R^3$ and $R^4$ are both hydrogen; and
$R^5$, $R^6$, $R^7$, $R^8$ and $R^9$ are all hydrogen; and
n is 4.

4. A compound according to claim 1, wherein said compound is selected from the group consisting of:
H-Dmt-D-Arg-Phe-Lys-$NH_2$;
H-Dmt-D-Arg-Phe-Orn-$NH_2$;
H-Dmt-D-Arg-Phe-$A_2$Bu-$NH_2$, wherein $A_2$Bu is α,γ-diaminobutyryic acid
H-Mmt-D-Arg-Phe-Lys-$NH_2$;
H-Dmt-D-Arg-Phe(p-F)-Lys-$NH_2$; and
Dmt(NMe)-D-Arg-Phe-Lys-$NH_2$.

5. A salt of a compound according to claim 1 selected from the group consisting of: a hydrochloride, an acetate, or a trifluoroacetate salt.

6. A pharmaceutical composition comprising a compound according to claim 1 as an active ingredient, in admixture with one or more pharmaceutically acceptable carriers.

7. A process for preparing a compound of formula I according to claim 1, comprising:
   a) preparing a peptide attached to a solid phase support;
   b) coupling a protected amino acid to said peptide in an inert solvent using a coupling agent;
   c) completing the synthesis; and
   d) isolating the compound of formula I.

8. A method for treating a patient suffering from pain, comprising administering to said patient a compound according to claim 1 for a time and under conditions effective to induce analgesia.

9. A method for treatment according to claim 8, wherein the pain is labor pain.

* * * * *

UNITED STATES PATENT AND TRADEMARK OFFICE
Certificate

Patent No. 6,703,483 B1                                               Patented: March 9, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Peter Schiller, Montreal, Quebec, Canada, and Hazel Szeto, New York, NY.

Signed and Sealed this Eighteenth Day of May 2004.

<div style="text-align: right;">
CHRISTOPHER LOW<br>
*Supervisory Patent Examiner*<br>
Art Unit 1653
</div>

UNITED STATES PATENT AND TRADEMARK OFFICE
CERTIFICATE OF CORRECTION

PATENT NO. : 6,703,483 B1
DATED : March 9, 2004
INVENTOR(S) : Schiller et al.

It is certified that error appears in the above-identified patent and that said Letters Patent is hereby corrected as shown below:

Column 1,
Prior to line 15, the following text is inserted"

-- STATEMENT OF GOVERNMENT FUNDING

This invention was made with Government support from the National Institute on Drug Abuse under Grant No. P01 DA08924. The Government has certain rights in this invention. --

Signed and Sealed this

Tenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,703,483 B1 Page 1 of 7
APPLICATION NO. : 09/590165
DATED : March 8, 2000
INVENTOR(S) : Schiller et al.

It is certified that error appears in the above-identified patent and that said Letters Patent is hereby corrected as shown below:

On the title page:
Item (75) should read --Peter Schiller, Montreal, Quebec, Canada: Hazel Szeto, New York, NY--

Signed and Sealed this

First Day of July, 2008

JON W. DUDAS
*Director of the United States Patent and Trademark Office*

(12) United States Patent
Schiller et al.

(10) Patent No.: US 6,703,483 B1
(45) Date of Patent: Mar. 9, 2004

(54) COMPOUNDS USEFUL IN PAIN MANAGEMENT

(75) Inventors: Peter Schiller, Montreal, Quebec (CA); Hazel Szeto, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/590,165
(22) PCT Filed: Mar. 8, 2000
(86) PCT No.: PCT/SE00/00462
§ 371 (c)(1),
(2), (4) Date: Jun. 9, 2000
(87) PCT Pub. No.: WO00/55189
PCT Pub. Date: Sep. 21, 2000

(30) Foreign Application Priority Data

Mar. 16, 1999 (SE) .................. 9900961

(51) Int. Cl.$^7$ .................. C07K 5/10
(52) U.S. Cl. .................. 530/330; 514/18
(58) Field of Search .................. 530/330; 514/18

(56) References Cited

U.S. PATENT DOCUMENTS

| | | | |
|---|---|---|---|
| 5,312,899 A | * | 5/1994 | Schiller .................. 530/331 |
| 5,602,100 A | * | 2/1997 | Brown .................. 514/18 |
| 5,885,958 A | * | 3/1999 | Zadina .................. 514/9 |
| 5,994,372 A | * | 11/1999 | Yaksh .................. 514/327 |

FOREIGN PATENT DOCUMENTS

WO  WO 95/22557  8/1995

OTHER PUBLICATIONS

Clapp, et al., "Cardiovascular and Metabolic Responses to Two Receptor-Selective Opioid Agonists in Pregnant Sheep," *Am. J. Obstet. Gynecol.* 178:397–401 (1998).

DiMaio, et al., "Synthesis and Pharmacological Characterization in Vitro of Cyclic Enkephalin Analogues: Effect of Conformational Constraints on Opiate Receptor Selectivity," *J. Med. Chem.* 25:1432–1438 (1982).

Majer, et al., "Synthesis of Methylated Phenylalanines Via Hydrogenolysis of Corresponding 1,2,3,4-Tetrahydroisoquinoline-3-Carboxylic Acids," *Int. J. Peptide Protein Res.* 43:62–68 (1994).

Schiller, et al., "Dermorphin Analogues Carrying an Increased Positive Net Charge in Their 'Message' Domain Display Extremely High μ Opioid Receptor Selectivity," *J. Med. Chem.* 32:698–703 (1989).

Schiller, et al., "TIPP[ψ]: A Highly Potent and Stable Pseudopeptide δ Opioid Receptor Antagonist with Extraordinary δ Selectivity," *J. Med. Chem.* 36:3182–3187 (1993).

Schiller, et al., "Unsulfated C-Terminal 7-Peptide of Cholecystokinin: A New Ligand of the Opiate Receptor," *Biochem. Biophys. Res. Comm.* 85:1332–1338 (1978).

Schiller, et al., "Opioid Peptide Analogs with Novel Activity Profiles as Potential Therapeutic Agents for use in Analgesia," *Pept. Sci.: Present Future, Proc. 1st Int. Pept. Symp.* (1999), Meeting Date 1997, 665–669.

* cited by examiner

Primary Examiner—Christopher S. F. Low
Assistant Examiner—David Lukton
(74) Attorney, Agent, or Firm—Michael A. Sanzo; Fitch, Even, Tabin & Flannery

(57) ABSTRACT

Compounds of the formula I

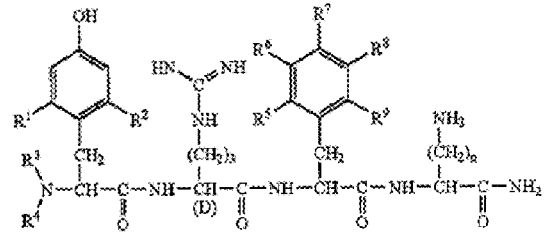

are disclosed and claimed in the present application, as well as their pharmaceutically acceptable salts, pharmaceutical compositions, comprising the novel compounds and their use in therapy, particular in the management of pain, and more particularly in the management of pain during labor.

9 Claims, No Drawings

COMPOUNDS USEFUL IN PAIN MANAGEMENT

STATEMENT OF GOVERNMENT FUNDING

This invention was made with Government support from the National Institute on Drug Abuse under Grant No. P01 DA08924. The Government has certain rights in this invention.

CROSS REFERENCE TO RELATED APPLICATIONS

The present application represents U.S. national stage of international application PCT/SE00/00462, with an international filing date of Mar. 8, 2000, and which was published in English under Article 21(2) of the PCT on Sep. 21, 2000. The international application claims priority to Swedish application 9900961-5, filed Mar. 16, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain during labor.

BACKGROUND AND PRIOR ART

Although a wide spectrum of narcotics are now available, only a few are used currently in obstetrics, including morphine, pethidine, fentanyl and sufentanil. These narcotics can cause a variety of side effects in the mother, including respiratory depression, and orthostatic hypotension. Furthermore, because of their lipophilic character, these opiate analgesics are transferred rapidly across the placenta and often produce neonatal respiratory depression and changes in the neurobehavior of the child. While these side effects are particularly pronounced when lipophilic opiates are administered systemically, they are still of some concern with the delivery of classical narcotics by the spinal or epidural route which were introduced in 1979 and are now widely accepted for obstetric analgesia.

Opioid peptides and their analogs have a reduced ability to cross the placental barrier because of their polar character. A number of opioid peptide analogs with high selectivity for μ opioid receptors and μ agonist properties have been developed (for a review, see P. W. Schiller, in *"Progress in Medicinal Chemistry"*, Vol. 28 (G. P. Ellis and G. B. West, eds.), Elsevier, Amsterdam, The Netherlands, 1991, pp. 301-340). Among these, the dermorphin related tetrapeptide analog H-Tyr-D-Arg-Phe-Lys-$NH_2$ (DALDA) is particularly polar (P. W. Schiller et al., *J. Med. Chem.* 32, 698-703 (1989)). DALDA is also disclosed and claimed in U.S. Pat. No. 5,312,899, granted 17 May 1994 to P. W. Schiller and now assigned to the Applicant of the present application. DALDA shows high μ receptor affinity and excellent μ receptor selectivity in the rat brain membrane binding assay as well as considerable μ agonist potency in the functional guinea pig ileum (GPI) bioassay. However, like morphine, DALDA did produce delayed respiratory depression (2 h after i.th. administration) at a dose of 7.5 μg (32×ED50).

The problem underlying the present invention was thus to provide novel compounds with improved μ agonist potency, as well as with as few side-effects as possible. More particularly the object of the invention was to improve the potency as well as the side-effect profile for compounds used particularly within the obstetrics field.

Outline of the Invention

The present invention is directed to novel analogs of DALDA, defined by the formula I

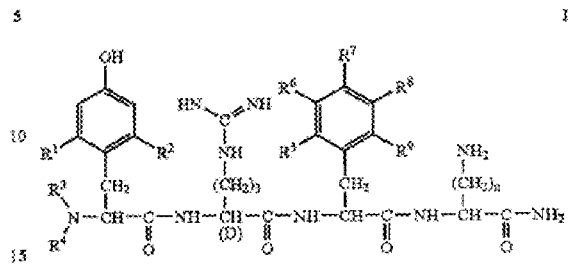

wherein
$R^1$ is selected from
  (i) linear or branched $C_1$-$C_6$ alkyl;
  (ii) $C_1$-$C_6$ alkoxy;
$R^2$ is selected from
  (i) hydrogen;
  (ii) linear or branched $C_1$-$C_6$ alkyl;
  (iii) $C_1$-$C_6$ alkoxy;
$R^3$ and $R^4$ is each and independently selected from
  (i) hydrogen;
  (ii) linear or branched $C_1$-$C_6$ alkyl;

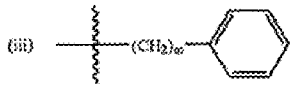

wherein m=1-3;

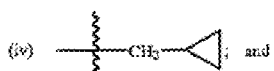

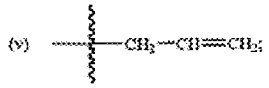

$R^5$, $R^6$, $R^7$, $R^8$ and $R^9$ is each and independently selected from
  (i) hydrogen;
  (ii) halogen, where "halogen" encompasses chloro, fluoro, bromo and iodo; and
  (iii) linear or branched $C_1$-$C_6$ alkyl; and
n is an integer of from 1 to 5.

In a preferred embodiment of the present invention
$R^1$ is a linear $C_1$-$C_6$ alkyl;
$R^2$ is a linear $C_1$-$C_6$ alkyl or hydrogen;
$R^3$ and $R^4$ is each and independently selected from a straight $C_1$-$C_6$ alkyl or hydrogen;
$R^5$, $R^6$, $R^7$, $R^8$ and $R^9$ is each and independently selected from
  (i) hydrogen;
  (ii) halogen, where "halogen" encompasses chloro, fluoro, bromo and iodo;
  (iii) linear or branched $C_1$-$C_6$ alkyl; and
n is an integer of from 1 to 5.

In particularly preferred embodiment of the present invention
$R^1$ is $CH_3$;
$R^2$ is hydrogen or $CH_3$;
$R^3$ and $R^4$ are both hydrogen; and $R^5$, $R^6$, $R^7$, $R^8$ and $R^9$ are all hydrogen; and
n is 4.

Within the scope of the invention are also pharmaceutically acceptable salts of the compounds of the formula I.

Suitable pharmaceutically acceptable salts of the compounds of formula I are the hydrochloride salt, the acetate salt and the trifluoroacetate salt.

The novel compounds of the present invention, which compounds are DALDA analogs, are useful in therapy, especially as analgesics, and particularly as analgesics within the field of obstetrics. The wording "analgesics" is defined as absence of pain in response to stimulation which would normally be painful.

Also within the scope of the invention is the use of a compound of the formula I above, for the manufacture of a medicament for use as an analgesic, particularly as an analgesic within the field of obstetrics, more particularly for use in the treatment of pain during labor.

A further aspect of the invention is a method for the treatment of a subject suffering from pain, particularly pain during labor, whereby an effective amount of a compound of the formula I above, is administered to a patient in need of pain relief.

Methods of Preparation

The compounds of the present invention may be prepared as described in the following.

Most Boc-amino acid derivatives used in the peptide syntheses are commercially available (Bachem Bioscience and RSP Amino Acid Analogues). 2-methyl-L-tyrosine (Mmt) was prepared by hydrogenolysis of 7-hydroxytetrahydroisoquinoline-3-carboxylic acid using Pd/H$_2$ as described by P. Majer et al., *Int. J. Peptide Protein Res.* 43, 62–68 (1994).

All peptides were prepared by solid-phase techniques. The p-methylbenzhydrylamine resin was used for the solid-phase synthesis of the peptides which all contain a C-terminal carboxamide group. Boc protection of the amino group was employed in the preparation of all peptides. The syntheses were performed according to protocols that have been extensively used in the inventor's laboratory (P. W. Schiller et al., *J. Med. Chem.* 36, 3182–3187 (1993)). Couplings were performed in a mixture of CH$_2$Cl$_2$/DMF (95:5; v/v), using 1,3-diisopropylcarbodiimide (DIC)/1-hydroxybenzotriazole (HOBt) as coupling agents. Completeness of coupling was carefully examined after each coupling step by means of the ninhydrin color test. The fully assembled peptide was cleaved from the resin and completely deprotected by treatment with liquid HF at 0° C. and in the presence of anisole as scavenger (60–90 min).

The HPLC system GOLD (Beckman) consisting of the programmable solvent module 126 and the diode array detector module 168 was used in the purification and the purity control of the peptides. Reversed-phase HPLC was performed using a gradient made from two solvents: (A) 0.1% TFA in water and (B) 0.1% TFA in acetonitrile. For preparative runs a Vidac 218TP1022 column (250×22 mm) was used with a linear gradient of 5–20% B over a period of 30 min at a flow rate of 7 ml/min, absorptions being measured at both 216 nm and 280 nm. The same gradient was used for analytical runs on a Vidac 218TP0046 column (250×4.6 mm) over a period of 30 min at a flow rate of 1.0 ml/min. Purity of peptides was also established by TLC on precoated silica gel plates 60F-254 (E. Merck, Darmstadt, Germany) in the following solvent systems (all v/v): (A) n-BuOH/AcOH/H$_2$O (4:1:5, organic phase) and (B) n-BuOH/pyridine/AcOH/H$_2$O (15:10:3:12). Peptides were visualized with UV and with the ninhydrin spray reagent. Molecular weights of peptides were determined by FAB mass spectrometry on an MS-50 HMTCTA mass spectrometer interfaced with a DS-90 data system.

EXAMPLES

The invention will now be described in more detail by way of the following Examples, which are not to be construed as limiting the invention in any way.

Example 1
Preparation of H-Dmt-D-Arg-Phe-Lys-NH$_2$

Benzhydrylamine resin (1 g, 0.54 meq/g resin, Bachem Bioscience) was washed with reagents in the following sequence: CH$_2$Cl$_2$ (3×1 min), 10% (v/v) DIEA in CH$_2$Cl$_2$ (2×5 min), CH$_2$Cl$_2$ (5×1 min). Boc-Lys(2-Cl-Z) (560 mg, 1.35 mmol) was then coupled using HOBt (182 mg, 1.35 mmol) and DIC (170 mg, 1.35 mmol) in CH$_2$Cl$_2$/DMF (95:5, v/v) for 3 h. The resin was then washed with CH$_2$Cl$_2$ (3×1 min), EtOH (1 min) and CH$_2$Cl$_2$ (3×1 min). The resin was then treated with 50% (v/v) TFA in CH$_2$Cl$_2$ (30 min). This sequence of washes and reactions was repeated for the addition of each of the residues. The following side chain-protected Boc-amino acids were used: Boc-D-Arg(Tos)-OH and Boc-Dmt-OH. After final deprotection with 50% (v/v) TFA in CH$_2$Cl$_2$ (30 min), the resin was washed with CH$_2$Cl$_2$ (3×1 min) and ETOH (3×1 min) and was dried in a dessicator. The dry resin was treated with 20 ml of HF plus 1 ml of anisole first for 90 min at 0° C. and then for 15 min at room temperature. After evaporation of the HF, the resin was extracted three times with Et$_2$O and, subsequently three times with 1M AcOH. The crude peptide was then obtained in solid form through lyophilization of the combined acetic acid extracts. The peptide was purified by HPLC on a Vidac 218TP1022 column (250×22 mm) with a linear gradient of 5–20% acetonitrile in 0.1% TFA. After solvent evaporation the pure peptide was dissolved in conc. AcOH and was obtained in solid form through lyophilization.

Yield: 200 mg (61%)
FAB-MS: MH$^+$=639
TLC (silica): R$_f$=0.15 (A); R$_f$=0.28 (B)
HPLC: k'=2.05

Examples 2–4

By following the same procedure as described in Example 1 above, the compounds shown in Table 1 were also prepared.

TABLE 1

| Example | Compound | Molecular weight FAB-MS [MH$^+$] |
|---|---|---|
| 2 | H-Dmt-D-Arg-Phe-Orn-NH$_2$ | 625 |
| 3 | H-Dmt-D-Arg-Phe-A$_3$bu-NH$_2$ | 611 |
| 4 | H-Mmt-D-Arg-Phe-Lys-NH$_2$ | 625 |
| 5 | H-Dmt-D-Arg-Phe(p-F)-Lys-NH$_2$ | 657 |
| 6 | Dmt(NMe)-D-Arg-Phe-Lys-NH$_2$ | 653 |

Pharmaceutical Compositions

Also with the scope of the present invention, are pharmaceutical compositions comprising a compound of formula I or a salt thereof as active ingredient, in admixture with one or more pharmaceutically acceptable carriers.

Suitable pharmaceutical compositions according to the present invention are pharmaceutical compositions in liquid form, suitable for administration intrathecally, epidurally, intramuscularly, and intravenously. Infusion is particularly preferred.

The dosage will depend on the severity of the pain, the patient's weight and other factors normally considered by the attending physician when determining the individual regimen and dosage level as the most appropriate for a particular patient.

Biological Evaluation
Pharmacologic Testing in Vitro of μ Opioid Agonists Bioassays based on inhibition of electrically evoked contractions of the guinea pig ileum (GPI) and mouse vas deferens (MVD) were performed. In the GPI assay the opioid effect is primarily mediated by μ receptors, whereas in the MVD assay the inhibition of the contractions is mostly due to interaction with δ opioid receptors. Agonist potencies are expressed as IC50 values (concentration of the agonist that produces 50% inhibition of the electrically induced contraction).

Bioassays Using Isolated Organ Preparations

The GPI and MVD bioassays were carried out as reported in P. W. Schiller et al., *Biochem. Biophys. Res. Commun.* 85, 1332-1338 (1978) and J. DiMaio et al., *J. Med. Chem.* 25, 1432-1438 (1982). A log-dose/response curve was determined with [Leu$^5$]enkephalin as standard for each ileum and vas preparation, and IC50 values of the compounds being tested were normalized according to A. A. Waterfield et al., *Eur. J. Pharmacol.* 58, pp. 11-18 (1997).

Opioid Receptor Binding Assays

μ and δ receptor binding constants ($K_i^\mu$, $K_i^\delta$) of the compounds were determined by displacement of relatively selective μ and δ radioligands from binding sites in rat brain membrane preparations (calculated from the measured IC50 values on the basis of the equation by Cheng and Prusoff (Y. C. Cheng and W. H. Prusoff (*Biochem. Pharmacol.* 22, 3099-3102, 1973)). The ratio $K_i^\delta/K_i^\mu$ was a quantitative measure of the μ versus δ receptor selectivity. κ receptor binding constants were determined by displacement of a κ receptor-selective radioligand from guinea pig brain membrane preparations, since the relative proportion of κ binding sites is higher in guinea pig brain that in rat brain.

Opioid Receptor Binding Experiments

The experimental procedure used represents a modified version of the binding assay described by Pasternak et al. (*Mol. Pharmacol.* 11, 340-351 (1975)). Male Sprague-Dawley rats (300-350 g) from the Canadian Breeding Laboratories were decapitated and after removal of the cerebellum the brains were homogenized in 30 volumes of ice-cold standard buffer (50 mM Tris HCl, pH 7.7). After centrifugation at 30,000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1-2 h at 25° C. with 1 ml standard buffer containing the peptide to be tested and one of the following radioligands at the final concentration indicated: [3]DAMGO, μ-selective, 0.7 nM; [$^3$H] DSLET, δ-selective, 1.0 nM; and [$^3$H]U69,563, κ-selective, 0.5 nM. The incubation was terminated by filtration through Whatman GF/B filters under vacuum at 4° C. Following two washings with 5 ml portions of ice-cold buffer the filters were transferred to scintillation vials and treated with 1 ml Protosol (New England Nuclear) for 30 min prior to addition of 0.5 ml acetic acid and 10 ml Aquasol (New England Nuclear). After shaking for 30 min the vials were counted at an efficiency of 40-45%. All experiments were performed in duplicate and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of the specific binding were obtained graphically from semi-logarithmic plots. From the measured IC50-values, binding inhibition constants ($K_i$) were calculated based on Cheng and Prusoff's equation. Ratios of the $K_i$-values determined in the μ-, δ- and κ-representative binding assays are a measure of the receptor selectivity of the compound under investigation (e.g. $K_i^\delta/K_i^\mu$ indicates the selectivity for μ-receptors versus δ-receptors).

Analgesic Testing

The rat tail flick test was used to assess the antinociceptive effect of the compounds after intrathecal (i.th.) administration. Male Sprague-Dawley rats (300-350 g) were used. For the spinal administration of the compounds to the rat, a catheter was placed in the intrathecal space. Under general anesthesia, a PE-10 tube was threaded to the level of the lumbosacral spinal cord, as described in the literature (N. Shimoyama et al., *Anesthesiology* 85, 1357-1366 (1996)). Methylene blue staining and dissection at the end of the study confirmed the correct placement of the catheter.

In the tail flick test the antinociceptive potency of the compounds was determined by cumulative dose-response analysis (N. Shimoyama et al., *J. Pharmacol. Exp. Ther.* 283, 648-652 (1997)). Intrathecal doses of each drug were delivered in a volume of 5 μl followed by 10 μl of saline to flush the catheter. A tail-flick apparatus (EMDIE, Richmond, Va.) was used to apply radiant heat at 5 to 8 cm from the tip of the tail. The time from the onset of the heat stimulus to the withdrawal of the tail (tail-flick latency) was measured. The intensity of the radiant heat was adjusted such that the base-line latencies were between 2.5 and 3.5 sec. Subsequent response latencies were determined at 15 min after spinal delivery of the compound. To avoid tissue damage the heat stimulus was turned off after 10 sec (cut-off latency). After measuring the base-line latencies, increasing doses of the compound to be tested were administered until each animal became an analgesic responder (cumulative dose-response assessment, as described by K. Elliott et al., *Pain* 59, 361-368 (1994)) or reached the highest test dose. An analgesic responder was defined as one whose response tail-flick latency was 2 or more times the value of the base-line latency. The latency data were converted to a quantal form by determining the percentage of analgesic responders in each group for each cumulative dose, and a dose-response curve was constructed for each compound. The quantal dose-response data were analyzed with the BLISS-21 computer program. This program maximized the log-likelihood function to fit a Gaussian normal sigmoid curve to the dose-response data and provided the ED50 value and a 95% confidence interval (CI) (J. G. Umans and C. E. Inturrisi, *J. Pharmacol. Exp. Ther.* 218, 409-415 (1981)).

Respiratory Depression Studies (Whole Body Plethysmography)

Whole body plethysmography was performed as described in the literature (K. Tatsumi et al., *J. Appl. Physiol.* 71, 37-42 (1991)). An unrestrained rat was placed in a 3-liter whole-body plethysmograph chamber and breathed 100% humidified air supplied into and out of the chamber at a rate of 1000 ml/min. After a 15-min acclimation period the inlet and outlet of the chamber were closed and the pressure changes in the box, caused by the warming and wetting of the gas inspired by the rat and the cooling and drying of the expired gas, were recorded using a high-gain differential pressure transducer. A calibration volume of 0.2 ml of air was regularly introduced into the chamber during the recordings. The recordings were made for 20-30 seconds. Subsequently, the inlet and outlet were opened, and the gas supply was changed to a mixture of 5% $CO_2$ and 21% $O_2$ in $N_2$ (100% humidified) and the rat was allowed to breathe the gas mixture for 5 min to reach a steady-state ventilatory condition. The recordings of changes in pressure were repeated with the chamber closed. Tidal volumes were calculated from the pressure changes using the equation derived by J. E. Drorbaugh and W. O. Fenn, *Pediatrics* 16, 81-87 (1955). Respiratory frequencies were also determined from the number of respiratory cycles in the recordings and minute ventilations were calculated (tidal volume× frequency).

Compounds were administered at a low dose (3×ED50 determined in the analgesic test) and at a high dose (30× ED50). The high dose of morphine and both the low and the high dose of DALDA significantly decreased minute ventilation by 26%, 26% and 30%, respectively, during a period of 3 to 6 hours after i.th. administration. Neither dose of H-Dmt-D-Arg-Phe-Lys-$NH_2$ significantly decreased minute ventilation as compared to the control value determined with saline.

In Vivo Disposition in Pregnant Sheep

The in vivo disposition after i.v. administration to pregnant sheep was examined by using procedures described in the literature (H. H. Szeto et al., *J. Pharmacol. Exp. Ther.* 284, 61-65 (1998)). Chronic indwelling catheters were surgically placed in four pregnant ewes (gestional age, 115-120 days; term ~145 days) as described by H. H. Szeto et al., *Am. J. Physiol.* 258, R1453-R1458 (1990). One polyvinyl catheter was inserted into the femoral artery and advanced to the distal aorta for blood sampling and another was advanced into the inferior vena cava via the femoral vein for drug infusion. A fetal hindlimb was exposed via hysterotomy incision, and chronic indwelling catheters were also placed in the fetal distal aorta and inferior vena cava. The compounds according to the invention were administered as a constant-rate intravenous infusion (0.6 mg/kg/h and 0.06 mg/kg/h, respectively, for 4 h) to the sheep, and blood samples were collected at 0, 1, 2, 3, 3.5, 4, 4.25, 4.5, 5, 6, 7, 12 and 24 h. Blood samples were collected form the fetus at 0, 3, 3.5, 4, 5 and 6 h. All blood samples were collected into chilled borosilicate glass tubes containing EDTA and centrifuged, and the plasma was stored in glass containers with Teflon-lined caps and frozen at $-80°$ C.

The compounds were quantified by using reversed-phase HPLC and MS detection, as described by Grigoriants et al., *J. Chromatogr. B, Biomedical Applications* 695, 287-298 (1997). Plasma samples were deproteinated and eluted through a solid-phase extraction cartridge (Sep-Pak C18; Millipore) with $CH_3CN$. An internal standard, the deuterated DALDA analog H-Tyr-D-Arg-Phe($d_5$)-Lys-$NH_2$, or a deuterated analog of a compound according to the invention, was added to each plasma sample before deproteinization. The filtered plasma sample was chromatographed on an RP-analytical column (Delta Pak, 5 μm, C18, 100 Å, 150× 3.9 mm; Waters, Milford, Mass.) at a flow rate of 1.5 ml/min, and UV absorption was monitored at 200 nm. One-minute fractions were collected and each fraction was lyophilized for MS analysis (Auto SpecQ tandem mass spectrometer, Micromass, Altrincham, UK). Continuous flow-LSIMS was used to quantify DALDA. The $(M+H)^+$ ion current for DALDA at m/z 612 was compared with the ion current from $d_5$-DALDA at m/z 617, and the one for the DALDA analog at its m/z value was compared with the one from the deuterated DALDA-analog. The limit of sensitivity of this method is 50 ng/ml DALDA or DALDA analog.

Neither of the peptides was detected in any of the fetal plasma samples. In other words, DALDA and its analogs according to the present invention, do not cross the placental barrier to a significant extent.

Hemodynamic and Metabolic Effects of DALDA and its Analogs in the Pregnant Sheep Model Using the same instrumented pregnant sheep model described above, DALDA and its analogs were administered by i.v. infusion at a dose of 0.6 mg/kg/h and 0.06 mg/kg/h, respectively. No effect on maternal blood pressure, heart rate, blood gases and plasma glucose were observed. Similarly, neither peptide had any effect on fetal blood pressure, heart rate, blood gases and plasma glucose.

The best mode of performing the invention known at present is the use of the compound according to Example 1.

Abbreviations $A_2Bu$=α,γ-diaminobutyric acid
Boc=tert-butoxycarbonyl
CI=confidence interval
DALDA=H-Tyr-D-Arg-Phe-Lys-$NH_2$
DAMGO=H-Tyr-D-Ala-Gly-Phe($N_\alpha$Me)-Gly-ol
DIC=1,3-diisopropylcarbodiimide
Dmt=2',6'-dimethyltyrosine
DSLET=H-Tyr-D-Ser-Gly-Phe-Leu-Thr-OH
EDTA=ethylenediaminetetraacetic acid
FAB-MS=fast atom bombardment mass spectrometry
GPI=guinea pig ileum
HOBt=1-hydroxybenzotriazole
HPLC=high performance liquid chromatography
i.th.=intrathecal
LSIMS=liquid secondary ion mass spectrometry
Mmt=2'-methyltyrosine
MS=mass spectrometry
MVD=mouse vas deferens
TFA=trifluoroacetic acid
TLC=thin layer chromatography
Tos=tosyl
U69,593=(5α, 7α, 8β)-(−)-N-methyl-[7-pyrrolidinyl)-1-oxaspiro[4,5]dec-8-yl]benzeneacetamide

What is claimed is:

1. A compound of formula I:

(I)

wherein $R^1$ is selected from
  (i) a linear or branched $C_1$-$C_6$ alkyl;
  (ii) a $C_1$-$C_6$ alkoxy;

$R^2$ is selected from
(i) hydrogen;
(ii) a linear or branched $C_1$-$C_6$ alkyl;
(iii) a $C_1$-$C_6$ alkoxy;

$R^3$ and $R^4$ is each and independently selected from
(i) hydrogen;
(ii) a linear or branched $C_1$-$C_6$ alkyl;

(iii) 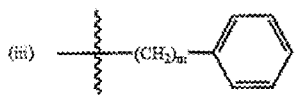

wherein m=1-3;

(iv) 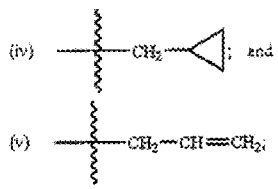

$R^5$, $R^6$, $R^7$, $R^8$ and $R^9$ is each and independently selected from
(i) hydrogen;
(ii) a halogen, where said halogen is selected from the group consisting of: chloro, fluoro, bromo and iodo; and
(iii) a linear or branched $C_1$-$C_6$ alkyl; and n is an integer of from 1 to 5;

or a pharmaceutically acceptable salt thereof.

2. A compound of formula I according to claim 1, wherein
$R^1$ is a linear $C_1$-$C_6$ alkyl;
$R^2$ is a linear $C_1$-$C_6$ alkyl or hydrogen;
$R^3$ and $R^4$ is each and independently selected from a straight $C_1$-$C_6$ alkyl or hydrogen;
$R^5$, $R^6$, $R^7$, $R^8$ and $R^9$ is each and independently selected from
(i) hydrogen;
(ii) halogen, where "halogen" encompasses chloro, fluoro, bromo and iodo;
(iii) linear or branched $C_1$-$C_6$ alkyl; and n is an integer of from 1 to 5.

3. A compound according to claim 1, wherein
$R^1$ is $CH_3$;
$R^2$ is hydrogen or $CH_3$;
$R^3$ and $R^4$ are both hydrogen; and
$R^5$, $R^6$, $R^7$, $R^8$ and $R^9$ are all hydrogen; and
n is 4.

4. A compound according to claim 1, wherein said compound is selected from the group consisting of:
H-Dmt-D-Arg-Phe-Lys-$NH_2$;
H-Dmt-D-Arg-Phe-Orn-$NH_2$;
H-Dmt-D-Arg-Phe-$A_2$Bu-$NH_2$;
H-Mmt-D-Arg-Phe-Lys-$NH_2$;
H-Dmt-D-Arg-Phe(p-F)-Lys-$NH_2$; and
Dmt(NMe)-D-Arg-Phe-Lys-$NH_2$.

5. A salt of a compound according to claim 1 selected from the group consisting of: a hydrochloride, an acetate, or a trifluoroacetate salt.

6. A pharmaceutical composition comprising a compound according to claim 1 as an active ingredient, in admixture with one or more pharmaceutically acceptable carriers.

7. A process for preparing a compound of formula I according to claim 1, comprising:
a) preparing a peptide attached to a solid phase support;
b) coupling a protected amino acid to said peptide in an inert solvent using a coupling agent;
c) completing the synthesis; and
d) isolating the compound of formula I.

8. A method for treating a patient suffering from pain, comprising administering to said patient a compound according to claim 1 for a time and under conditions effective to induce analgesia.

9. A method for treatment according to claim 8, wherein the pain is labor pain.

* * * * *

UNITED STATES PATENT AND TRADEMARK OFFICE
CERTIFICATE OF CORRECTION

PATENT NO.        : 6,703,483 B1
APPLICATION NO. : 09/590165
DATED             : March 9, 2004
INVENTOR(S)       : Schiller et al.

It is certified that error appears in the above-identified patent and that said Letters Patent is hereby corrected as shown below:

On the title page:
Item (75) should read --Peter Schiller, Montreal, Quebec, Canada: Hazel Szeto, New York, NY--

This certificate supersedes the Certificate of Correction issued July 1, 2008.

Signed and Sealed this

Ninth Day of December, 2008

JON W. DUDAS
*Director of the United States Patent and Trademark Office*

United States Patent
Schiller et al.

(10) Patent No.: US 6,703,483 B1
(45) Date of Patent: Mar. 9, 2004

(54) COMPOUNDS USEFUL IN PAIN MANAGEMENT

(75) Inventors: Peter Schiller, Montreal, Quebec (CA); Hazel Szeto, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/590,165

(22) PCT Filed: Mar. 8, 2000

(86) PCT No.: PCT/SE00/00462

§ 371 (c)(1),
(2), (4) Date: Jun. 9, 2000

(87) PCT Pub. No.: WO00/55189

PCT Pub. Date: Sep. 21, 2000

(30) Foreign Application Priority Data

Mar. 16, 1999 (SE) .................................. 9900961

(51) Int. Cl.$^7$ ................................................ C07K 5/10
(52) U.S. Cl. .................................... 530/330; 514/18
(58) Field of Search ........................... 530/330; 514/18

(56) References Cited

U.S. PATENT DOCUMENTS

| | | | |
|---|---|---|---|
| 5,312,899 A | * 5/1994 | Schiller | 530/331 |
| 5,602,100 A | * 2/1997 | Brown | 514/18 |
| 5,885,958 A | * 3/1999 | Zadina | 514/9 |
| 5,994,372 A | * 11/1999 | Yaksh | 514/327 |

FOREIGN PATENT DOCUMENTS

WO   WO 95/22557   8/1995

OTHER PUBLICATIONS

Clapp, et al., "Cardiovascular and Metabolic Responses to Two Receptor-Selective Opioid Agonists in Pregnant Sheep," *Am. J. Obstet. Gynecol.* 178:397–401 (1998).

DiMaio, et al., "Synthesis and Pharmacological Characterization in Vitro of Cyclic Enkephalin Analogues: Effect of Conformational Constraints on Opiate Receptor Selectivity," *J. Med. Chem.* 25:1432–1438 (1982).

Majer, et al., "Synthesis of Methylated Phenylalanines Via Hydrogenolysis of Corresponding 1,2,3,4-Tetrahydroisoquinoline-3-Carboxylic Acids," *Int. J. Peptide Protein Res.* 43:62–68 (1994).

Schiller, et al., "Dermorphin Analogues Carrying an Increased Positive Net Charge in Their 'Message' Domain Display Extremely High µ Opioid Receptor Selectivity," *J. Med. Chem.* 32:698–703 (1989).

Schiller, et al., "TIPP[ψ]: A Highly Potent and Stable Pseudopeptide δ Opioid Receptor Antagonist with Extraordinary δ Selectivity," *J. Med. Chem.* 36:3182–3187 (1993).

Schiller, et al., "Unsulfated C-Terminal 7-Peptide of Cholecystokinin: A New Ligand of the Opiate Receptor," *Biochem. Biophys. Res. Comm.* 85:1332–1338 (1978).

Schiller, et al., "Opioid Peptide Analogs with Novel Activity Profiles as Potential Therapeutic Agents for use in Analgesia," *Pept. Sci.: Present Future, Proc. 1$^{st}$ Int. Pept. Symp.* (1999), Meeting Date 1997, 665–669.

* cited by examiner

*Primary Examiner*—Christopher S. F. Low
*Assistant Examiner*—David Lukton
(74) *Attorney, Agent, or Firm*—Michael A. Sanzo; Fitch, Even, Tabin & Flannery

(57) ABSTRACT

Compounds of the formula I

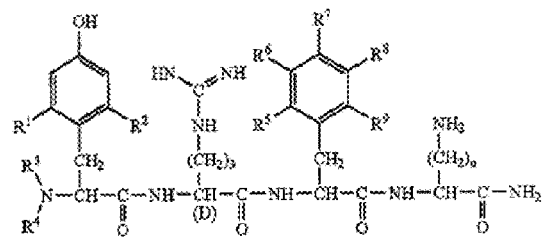

are disclosed and claimed in the present application, as well as their pharmaceutically acceptable salts, pharmaceutical compositions, comprising the novel compounds and their use in therapy, particular in the management of pain, and more particularly in the management of pain during labor.

9 Claims, No Drawings

COMPOUNDS USEFUL IN PAIN MANAGEMENT

STATEMENT OF GOVERNMENT FUNDING

This invention was made with Government support from the National Institute on Drug Abuse under Grant No. P01 DA08924. The Government has certain rights in this invention.

CROSS REFERENCE TO RELATED APPLICATIONS

The present application represents U.S. national stage of international application PCT/SE00/00462, with an international filing date of Mar. 8, 2000, and which was published in English under Article 21(2) of the PCT on Sep. 21, 2000. The international application claims priority to Swedish application 9900961-5, filed Mar. 16, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain during labor.

BACKGROUND AND PRIOR ART

Although a wide spectrum of narcotics are now available, only a few are used currently in obstetrics, including morphine, pethidine, fentanyl and sufentanil. These narcotics can cause a variety of side effects in the mother, including respiratory depression, and orthostatic hypotension. Furthermore, because of their lipophilic character, these opiate analgesics are transferred rapidly across the placenta and often produce neonatal respiratory depression and changes in the neurobehavior of the child. While these side effects are particularly pronounced when lipophilic opiates are administered systemically, they are still of some concern with the delivery of classical narcotics by the spinal or epidural route which were introduced in 1979 and are now widely accepted for obstetric analgesia.

Opioid peptides and their analogs have a reduced ability to cross the placental barrier because of their polar character. A number of opioid peptide analogs with high selectivity for μ opioid receptors and μ agonist properties have been developed (for a review, see P. W. Schiller, in *"Progress in Medicinal Chemistry"*, Vol. 28 (G. P. Ellis and G. B. West, eds.), Elsevier, Amsterdam, The Netherlands, 1991, pp. 301–340). Among these, the dermorphin related tetrapeptide analog H-Tyr-D-Arg-Phe-Lys-$NH_2$ (DALDA) is particularly polar (P. W. Schiller et al., *J. Med. Chem.* 32, 698–703 (1989)). DALDA is also disclosed and claimed in U.S. Pat. No. 5,312,899, granted 17 May 1994 to P. W. Schiller and now assigned to the Applicant of the present application. DALDA shows high μ receptor affinity and excellent μ receptor selectivity in the rat brain membrane binding assay as well as considerable μ agonist potency in the functional guinea pig ileum (GPI) bioassay. However, like morphine, DALDA did produce delayed respiratory depression (2 h after i.th. administration) at a dose of 7.5 μg (32×ED50).

The problem underlying the present invention was thus to provide novel compounds with improved μ agonist potency, as well as with as few side-effects as possible. More particularly the object of the invention was to improve the potency as well as the side-effect profile for compounds used particularly within the obstetrics field.

Outline of the Invention

The present invention is directed to novel analogs of DALDA, defined by the formula I

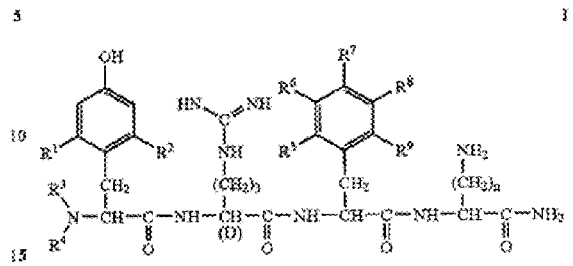

wherein
$R^1$ is selected from
(i) linear or branched $C_1$-$C_6$ alkyl;
(ii) $C_1$-$C_6$ alkoxy;
$R^2$ is selected from
(i) hydrogen;
(ii) linear or branched $C_1$-$C_6$ alkyl;
(iii) $C_1$-$C_6$ alkoxy;
$R^3$ and $R^4$ is each and independently selected from
(i) hydrogen;
(ii) linear or branched $C_1$-$C_6$ alkyl;

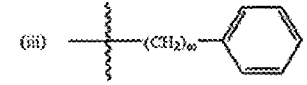

wherein m=1-3;

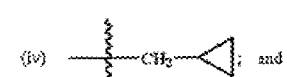

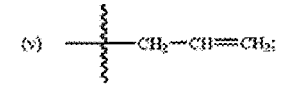

$R^5$, $R^6$, $R^7$, $R^8$ and $R^9$ is each and independently selected from
(i) hydrogen;
(ii) halogen, where "halogen" encompasses chloro, fluoro, bromo and iodo; and
(iii) linear or branched $C_1$-$C_6$ alkyl; and
n is an integer of from 1 to 5.

In a preferred embodiment of the present invention
$R^1$ is a linear $C_1$-$C_6$ alkyl;
$R^2$ is a linear $C_1$-$C_6$ alkyl or hydrogen;
$R^3$ and $R^4$ is each and independently selected from a straight $C_1$-$C_6$ alkyl or hydrogen;
$R^5$, $R^6$, $R^7$, $R^8$ and $R^9$ is each and independently selected from
(i) hydrogen;
(ii) halogen, where "halogen" encompasses chloro, fluoro, bromo and iodo;
(iii) linear or branched $C_1$-$C_6$ alkyl; and
n is an integer of from 1 to 5.

In particularly preferred embodiment of the present invention
$R^1$ is $CH_3$;
$R^2$ is hydrogen or $CH_3$;
$R^3$ and $R^4$ are both hydrogen; and $R^5$, $R^6$, $R^7$, $R^8$ and $R^9$ are all hydrogen; and
n is 4.

Within the scope of the invention are also pharmaceutically acceptable salts of the compounds of the formula I.

Suitable pharmaceutically acceptable salts of the compounds of formula I are the hydrochloride salt, the acetate salt and the trifluoroacetate salt.

The novel compounds of the present invention, which compounds are DALDA analogs, are useful in therapy, especially as analgesics, and particularly as analgesics within the field of obstetrics. The wording "analgesics" is defined as absence of pain in response to stimulation which would normally be painful.

Also within the scope of the invention is the use of a compound of the formula I above, for the manufacture of a medicament for use as an analgesic, particularly as an analgesic within the field of obstetrics, more particularly for use in the treatment of pain during labor.

A further aspect of the invention is a method for the treatment of a subject suffering from pain, particularly pain during labor, whereby an effective amount of a compound of the formula I above, is administered to a patient in need of pain relief.

Methods of Preparation

The compounds of the present invention may be prepared as described in the following.

Most Boc-amino acid derivatives used in the peptide syntheses are commercially available (Bachem Bioscience and RSP Amino Acid Analogues). 2-methyl-L-tyrosine (Mmt) was prepared by hydrogenolysis of 7-hydroxytetrahydroisoquinoline-3-carboxylic acid using Pd/H$_2$ as described by P. Majer et al., *Int. J. Peptide Protein Res.* 43, 62-68 (1994).

All peptides were prepared by solid-phase techniques. The p-methylbenzhydrylamine resin was used for the solid-phase synthesis of the peptides which all contain a C-terminal carboxamide group. Boc protection of the amino group was employed in the preparation of all peptides. The syntheses were performed according to protocols that have been extensively used in the inventor's laboratory (P. W. Schiller et al., *J. Med. Chem.* 36, 3182-3187 (1993)). Couplings were performed in a mixture of CH$_2$Cl$_2$/DMF (95:5; v/v), using 1,3-diisopropylcarbodiimide (DIC)/1-hydroxybenzotriazole (HOBt) as coupling agents. Completeness of coupling was carefully examined after each coupling step by means of the ninhydrin color test. The fully assembled peptide was cleaved from the resin and completely deprotected by treatment with liquid HF at 0° C. and in the presence of anisole as scavenger (60-90 min).

The HPLC system GOLD (Beckman) consisting of the programmable solvent module 126 and the diode array detector module 168 was used in the purification and the purity control of the peptides. Reversed-phase HPLC was performed using a gradient made from two solvents: (A) 0.1% TFA in water and (B) 0.1% TFA in acetonitrile. For preparative runs a Vidac 218TP1022 column (250×22 mm) was used with a linear gradient of 5-20% B over a period of 30 min at a flow rate of 7 ml/min, absorptions being measured at both 216 nm and 280 nm. The same gradient was used for analytical runs on a Vidac 218TP0046 column (250×4.6 mm) over a period of 30 min at a flow rate of 1.0 ml/min. Purity of peptides was also established by TLC on precoated silica gel plates 60F-254 (E. Merck, Darmstadt, Germany) in the following solvent systems (all v/v): (A) n-BuOH/AcOH/H$_2$O (4:1:5, organic phase) and (B) n-BuOH/pyridine/AcOH/H$_2$O (15:10:3;12). Peptides were visualized with UV and with the ninhydrin spray reagent. Molecular weights of peptides were determined by FAB mass spectrometry on an MS-50 HMTCTA mass spectrometer interfaced with a DS-90 data system.

EXAMPLES

The invention will now be described in more detail by way of the following Examples, which are not to be construed as limiting the invention in any way.

Example 1
Preparation of H-Dmt-D-Arg-Phe-Lys-NH$_2$

Benzhydrylamine resin (1 g, 0.54 meq/g resin, Bachem Bioscience) was washed with reagents in the following sequence: CH$_2$Cl$_2$ (3×1 min), 10% (v/v) DIEA in CH$_2$Cl$_2$ (2×5 min), CH$_2$Cl$_2$ (5×1 min). Boc-Lys(2-Cl-Z) (560 mg, 1.35 mmol) was then coupled using HOBt (182 mg, 1.35 mmol) and DIC (170 mg, 1.35 mmol) in CH$_2$Cl$_2$/DMF (95:5, v/v) for 3 h. The resin was then washed with CH$_2$Cl$_2$ (3×1 min), EtOH (1 min) and CH$_2$Cl$_2$ (3×1 min). The resin was then treated with 50% (v/v) TFA in CH$_2$Cl$_2$ (30 min). This sequence of washes and reactions was repeated for the addition of each of the residues. The following side chain-protected Boc-amino acids were used: Boc-D-Arg(Tos)-OH and Boc-Dmt-OH. After final deprotection with 50% (v/v) TFA in CH$_2$Cl$_2$ (30 min), the resin was washed with CH$_2$Cl$_2$ (3×1 min) and ETOH (3×1 min) and was dried in a dessicator. The dry resin was treated with 20 ml of HF plus 1 ml of anisole first for 90 min at 0° C. and then for 15 min at room temperature. After evaporation of the HF, the resin was extracted three times with Et$_2$O and, subsequently three times with 1M AcOH. The crude peptide was then obtained in solid form through lyophilization of the combined acetic acid extracts. The peptide was purified by HPLC on a Vidac 218TP1022 column (250×22 mm) with a linear gradient of 5-20% acetonitrile in 0.1% TFA. After solvent evaporation the pure peptide was dissolved in conc. AcOH and was obtained in solid form through lyophilization.

Yield: 200 mg (61%)
FAB-MS: MH$^+$=639
TLC (silica): R$_f$=0.15 (A); R$_f$=0.28 (B)
HPLC: k'=2.05

Examples 2-4

By following the same procedure as described in Example 1 above, the compounds shown in Table 1 were also prepared.

TABLE 1

| Example | Compound | Molecular weight FAB-MS [MH$^+$] |
|---|---|---|
| 2 | H-Dmt-D-Arg-Phe-Orn-NH$_2$ | 625 |
| 3 | H-Dmt-D-Arg-Phe-A$_2$bu-NH$_2$ | 611 |
| 4 | H-Mmt-D-Arg-Phe-Lys-NH$_2$ | 625 |
| 5 | H-Dmt-D-Arg-Phe(p-F)-Lys-NH$_2$ | 657 |
| 6 | Dmt(NMe)-D-Arg-Phe-Lys-NH$_2$ | 653 |

Pharmaceutical Compositions

Also with the scope of the present invention, are pharmaceutical compositions comprising a compound of formula I or a salt thereof as active ingredient, in admixture with one or more pharmaceutically acceptable carriers.

Suitable pharmaceutical compositions according to the present invention are pharmaceutical compositions in liquid form, suitable for administration intrathecally, epidurally, intramuscularly, and intravenously. Infusion is particularly preferred.

The dosage will depend on the severity of the pain, the patient's weight and other factors normally considered by the attending physician when determining the individual regimen and dosage level as the most appropriate for a particular patient.

Biological Evaluation
Pharmacologic Testing in Vitro of μ Opioid Agonists

Bioassays based on inhibition of electrically evoked contractions of the guinea pig ileum (GPI) and mouse vas deferens (MVD) were performed. In the GPI assay the opioid effect is primarily mediated by μ receptors, whereas in the MVD assay the inhibition of the contractions is mostly due to interaction with δ opioid receptors. Agonist potencies are expressed as IC50 values (concentration of the agonist that produces 50% inhibition of the electrically induced contraction).

Bioassays Using Isolated Organ Preparations

The GPI and MVD bioassays were carried out as reported in P. W. Schiller et al., *Biochem. Biophys. Res. Commun.* 85, 1332-1338 (1978) and J. DiMaio et al., *J. Med. Chem.* 25, 1432-1438 (1982). A log-dose/response curve was determined with [Leu$^5$]enkephalin as standard for each ileum and vas preparation, and IC50 values of the compounds being tested were normalized according to A. A. Waterfield et al., *Eur. J. Pharmacol.* 58, pp. 11-18 (1997).

Opioid Receptor Binding Assays

μ and δ receptor binding constants ($K_i^\mu$, $K_i^\delta$) of the compounds were determined by displacement of relatively selective μ and δ radioligands from binding sites in rat brain membrane preparations (calculated from the measured IC50 values on the basis of the equation by Cheng and Prusoff (Y. C. Cheng and W. H. Prusoff (*Biochem. Pharmacol.* 22, 3099-3102, 1973)). The ratio $K_i^\delta/K_i^\mu$ was a quantitative measure of the μ versus δ receptor selectivity. κ receptor binding constants were determined by displacement of a κ receptor-selective radioligand from guinea pig brain membrane preparations, since the relative proportion of κ binding sites is higher in guinea pig brain than in rat brain.

Opioid Receptor Binding Experiments

The experimental procedure used represents a modified version of the binding assay described by Pasternak et al. (*Mol. Pharmacol.* 11, 340-351 (1975)). Male Sprague-Dawley rats (300-350 g) from the Canadian Breeding Laboratories were decapitated and after removal of the cerebellum the brains were homogenized in 30 volumes of ice-cold standard buffer (50 mM Tris HCl, pH 7.7). After centrifugation at 30,000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1-2 h at 25° C. with 1 ml standard buffer containing the peptide to be tested and one of the following radioligands at the final concentration indicated: [3]DAMGO, μ-selective, 0.7 nM; [$^3$H] DSLET, δ-selective, 1.0 nM; and [$^3$H]U69,563, κ-selective, 0.5 nM. The incubation was terminated by filtration through Whatman GF/B filters under vacuum at 4° C. Following two washings with 5 ml portions of ice-cold buffer the filters were transferred to scintillation vials and treated with 1 ml Protosol (New England Nuclear) for 30 min prior to addition of 0.5 ml acetic acid and 10 ml Aquasol (New England Nuclear). After shaking for 30 min the vials were counted at an efficiency of 40-45%. All experiments were performed in duplicate and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of the specific binding were obtained graphically from semi-logarithmic plots. From the measured IC50-values, binding inhibition constants ($K_i$) were calculated based on Cheng and Prusoff's equation. Ratios of the $K_i$-values determined in the μ-, δ- and κ-representative binding assays are a measure of the receptor selectivity of the compound under investigation (e.g. $K_i^\delta/K_i^\mu$ indicates the selectivity for μ-receptors versus δ-receptors).

Analgesic Testing

The rat tail flick test was used to assess the antinociceptive effect of the compounds after intrathecal (i.th.) administration. Male Sprague-Dawley rats (300-350 g) were used. For the spinal administration of the compounds to the rat, a catheter was placed in the intrathecal space. Under general anesthesia, a PE-10 tube was threaded to the level of the lumbosacral spinal cord, as described in the literature (N. Shimoyama et al., *Anesthesiology* 85, 1357-1366 (1996)). Methylene blue staining and dissection at the end of the study confirmed the correct placement of the catheter.

In the tail flick test the antinociceptive potency of the compounds was determined by cumulative dose-response analysis (N. Shimoyama et al., *J. Pharmacol. Exp. Ther.* 283, 648-652 (1997)). Intrathecal doses of each drug were delivered in a volume of 5 μl followed by 10 μl of saline to flush the catheter. A tail-flick apparatus (EMDIE, Richmond, Va.) was used to apply radiant heat at 5 to 8 cm from the tip of the tail. The time from the onset of the heat stimulus to the withdrawal of the tail (tail-flick latency) was measured. The intensity of the radiant heat was adjusted such that the base-line latencies were between 2.5 and 3.5 sec. Subsequent response latencies were determined at 15 min after spinal delivery of the compound. To avoid tissue damage the heat stimulus was turned off after 10 sec (cut-off latency). After measuring the base-line latencies, increasing doses of the compound to be tested were administered until each animal became an analgesic responder (cumulative dose-response assessment, as described by K. Elliott et al., *Pain* 59, 361-368 (1994)) or reached the highest test dose. An analgesic responder was defined as one whose response tail-flick latency was 2 or more times the value of the base-line latency. The latency data were converted to a quantal form by determining the percentage of analgesic responders in each group for each cumulative dose, and a dose-response curve was constructed for each compound. The quantal dose-response data were analyzed with the BLISS-21 computer program. This program maximized the log-likelihood function to fit a Gaussian normal sigmoid curve to the dose-response data and provided the ED50 value and a 95% confidence interval (CI) (J. G. Umans and C. E. Inturrisi, *J. Pharmacol. Exp. Ther.* 218, 409-415 (1981)).

Respiratory Depression Studies (Whole Body Plethysmography)

Whole body plethysmography was performed as described in the literature (K. Tatsumi et al., *J. Appl. Physiol.* 71, 37-42 (1991)). An unrestrained rat was placed in a 3-liter whole-body plethysmograph chamber and breathed 100% humidified air supplied into and out of the chamber at a rate of 1000 ml/min. After a 15-min acclimation period the inlet and outlet of the chamber were closed and the pressure changes in the box, caused by the warming and wetting of the gas inspired by the rat and the cooling and drying of the expired gas, were recorded using a high-gain differential pressure transducer. A calibration volume of 0.2 ml of air was regularly introduced into the chamber during the recordings. The recordings were made for 20-30 seconds. Subsequently, the inlet and outlet were opened, and the gas supply was changed to a mixture of 5% $CO_2$ and 21% $O_2$ in $N_2$ (100% humidified) and the rat was allowed to breathe the gas mixture for 5 min to reach a steady-state ventilatory condition. The recordings of changes in pressure were repeated with the chamber closed. Tidal volumes were calculated from the pressure changes using the equation derived by J. E. Drorbaugh and W. O. Fenn, *Pediatrics* 16, 81-87 (1955). Respiratory frequencies were also determined from the number of respiratory cycles in the recordings and minute ventilations were calculated (tidal volume× frequency).

Compounds were administered at a low dose (3×ED50 determined in the analgesic test) and at a high dose (30× ED50). The high dose of morphine and both the low and the high dose of DALDA significantly decreased minute ventilation by 26%, 26% and 30%, respectively, during a period of 3 to 6 hours after i.th. administration. Neither dose of H-Dmt-D-Arg-Phe-Lys-$NH_2$ significantly decreased minute ventilation as compared to the control value determined with saline.

In Vivo Disposition in Pregnant Sheep

The in vivo disposition after i.v. administration to pregnant sheep was examined by using procedures described in the literature (H. H. Szeto et al., *J. Pharmacol. Exp. Ther.* 284, 61-65 (1998)). Chronic indwelling catheters were surgically placed in four pregnant ewes (gestional age, 115-120 days; term ~145 days) as described by H. H. Szeto et al., *Am. J. Physiol.* 258, R1453-R1458 (1990). One polyvinyl catheter was inserted into the femoral artery and advanced to the distal aorta for blood sampling and another was advanced into the inferior vena cava via the femoral vein for drug infusion. A fetal hindlimb was exposed via hysterotomy incision, and chronic indwelling catheters were also placed in the fetal distal aorta and inferior vena cava. The compounds according to the invention were administered as a constant-rate intravenous infusion (0.6 mg/kg/h and 0.06 mg/kg/h, respectively, for 4 h) to the sheep, and blood samples were collected at 0, 1, 2, 3, 3.5, 4, 4.25, 4.5, 5, 6, 7, 12 and 24 h. Blood samples were collected form the fetus at 0, 3, 3.5, 4, 5 and 6 h. All blood samples were collected into chilled borosilicate glass tubes containing EDTA and centrifuged, and the plasma was stored in glass containers with Teflon-lined caps and frozen at −80° C.

The compounds were quantified by using reversed-phase HPLC and MS detection, as described by Grigoriants et al., *J. Chromatogr. B, Biomedical Applications* 695, 287-298 (1997). Plasma samples were deproteinated and eluted through a solid-phase extraction cartridge (Sep-Pak C18; Millipore) with $CH_3CN$. An internal standard, the deuterated DALDA analog H-Tyr-D-Arg-Phe($d_5$)-Lys-$NH_2$ or a deuterated analog of a compound according to the invention, was added to each plasma sample before deproteinization. The filtered plasma sample was chromatographed on an RP-analytical column (Delta Pak, 5 μm, C18, 100 Å, 150× 3.9 mm; Waters, Milford, Mass.) at a flow rate of 1.5 ml/min, and UV absorption was monitored at 200 nm. One-minute fractions were collected and each fraction was lyophilized for MS analysis (Auto SpecQ tandem mass spectrometer, Micromass, Altrincham, UK). Continuous flow-LSIMS was used to quantify DALDA. The $(M+H)^+$ ion current for DALDA at m/z 612 was compared with the ion current from $d_5$-DALDA at m/z 617, and the one for the DALDA analog at its m/z value was compared with the one from the deuterated DALDA analog. The limit of sensitivity of this method is 50 ng/ml DALDA or DALDA analog.

Neither of the peptides was detected in any of the fetal plasma samples. In other words, DALDA and its analogs according to the present invention, do not cross the placental barrier to a significant extent.

Hemodynamic and Metabolic Effects of DALDA and its Analogs in the Pregnant Sheep Model Using the same instrumented pregnant sheep model described above, DALDA and its analogs were administered by i.v. infusion at a dose of 0.6 mg/kg/h and 0.06 mg/kg/h, respectively. No effect on maternal blood pressure, heart rate, blood gases and plasma glucose were observed. Similarly, neither peptide had any effect on fetal blood pressure, heart rate, blood gases and plasma glucose.

The best mode of performing the invention known at present is the use of the compound according to Example 1.

Abbreviations $A_2Bu$=α, γ-diaminobutyric acid
Boc=tert-butoxycarbonyl
CI=confidence interval
DALDA=H-Tyr-D-Arg-Phe-Lys-$NH_2$
DAMGO=H-Tyr-D-Ala-Gly-Phe($N_\alpha$Me)-Gly-ol
DIC=1,3-diisopropylcarbodiimide
Dmt=2',6'-dimethyltyrosine
DSLET=H-Tyr-D-Ser-Gly-Phe-Leu-Thr-OH
EDTA=ethylenediaminetetraacetic acid
FAB-MS=fast atom bombardment mass spectrometry
GPI=guinea pig ileum
HOBt=1-hydroxybenzotriazole
HPLC=high performance liquid chromatography
i.th.=intrathecal
LSIMS=liquid secondary ion mass spectrometry
Mmt=2'-methyltyrosine
MS=mass spectrometry
MVD=mouse vas deferens
TFA=trifluoroacetic acid
TLC=thin layer chromatography
Tos=tosyl
U69,593=(5α, 7α, 8β)-(−)-N-methyl-[7-pyrrolidinyl)-1-oxaspiro[4,5]dec-8-yl]benzeneacetamide

What is claimed is:

1. A compound of formula I:

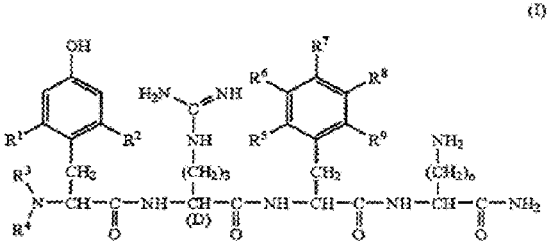

(I)

wherein $R^1$ is selected from
(i) a linear or branched $C_1$-$C_6$ alkyl;
(ii) a $C_1$-$C_6$ alkoxy;

$R^2$ is selected from
(i) hydrogen;
(ii) a linear or branched $C_1$-$C_6$ alkyl;
(iii) a $C_1$-$C_6$ alkoxy;
$R^3$ and $R^4$ is each and independently selected from
(i) hydrogen;
(ii) a linear or branched $C_1$-$C_6$ alkyl;

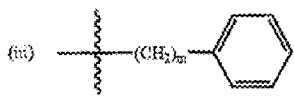

wherein m=1-3;

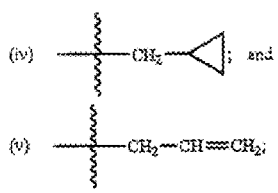

$R^5$, $R^6$, $R^7$, $R^8$ and $R^9$ is each and independently selected from
(i) hydrogen;
(ii) a halogen, where said halogen is selected from the group consisting of: chloro, fluoro, bromo and iodo; and
(iii) a linear or branched $C_1$-$C_6$ alkyl; and
n is an integer of from 1 to 5;
or a pharmaceutically acceptable salt thereof.

2. A compound of formula I according to claim 1, wherein
$R^1$ is a linear $C_1$-$C_6$ alkyl;
$R^2$ is a linear $C_1$-$C_6$ alkyl or hydrogen;
$R^3$ and $R^4$ is each and independently selected from a straight $C_1$-$C_6$ alkyl or hydrogen;
$R^5$, $R^6$, $R^7$, $R^8$ and $R^9$ is each and independently selected from
(i) hydrogen;
(ii) halogen, where "halogen" encompasses chloro, fluoro, bromo and iodo;
(iii) linear or branched $C_1$-$C_6$ alkyl; and
n is an integer of from 1 to 5.

3. A compound according to claim 1, wherein
$R^1$ is $CH_3$;
$R^2$ is hydrogen or $CH_3$;
$R^3$ and $R^4$ are both hydrogen; and
$R^5$, $R^6$, $R^7$, $R^8$ and $R^9$ are all hydrogen; and
n is 4.

4. A compound according to claim 1, wherein said compound is selected from the group consisting of:
H-Dmt-D-Arg-Phe-Lys-$NH_2$;
H-Dmt-D-Arg-Phe-Orn-$NH_2$;
H-Dmt-D-Arg-Phe-$A_2$Bu-$NH_2$;
H-Mmt-D-Arg-Phe-Lys-$NH_2$;
H-Dmt-D-Arg-Phe(p-F)-Lys-$NH_2$; and
Dmt(NMe)-D-Arg-Phe-Lys-$NH_2$.

5. A salt of a compound according to claim 1 selected from the group consisting of: a hydrochloride, an acetate, or a trifluoroacetate salt.

6. A pharmaceutical composition comprising a compound according to claim 1 as an active ingredient, in admixture with one or more pharmaceutically acceptable carriers.

7. A process for preparing a compound of formula I according to claim 1, comprising:
a) preparing a peptide attached to a solid phase support;
b) coupling a protected amino acid to said peptide in an inert solvent using a coupling agent;
c) completing the synthesis; and
d) isolating the compound of formula I.

8. A method for treating a patient suffering from pain, comprising administering to said patient a compound according to claim 1 for a time and under conditions effective to induce analgesia.

9. A method for treatment according to claim 8, wherein the pain is labor pain.

* * * * *